(12) United States Patent
Gum et al.

(10) Patent No.: US 9,403,035 B2
(45) Date of Patent: Aug. 2, 2016

(54) DOSE-OPTIMISED PATIENT POSITIONING FOR RADIOTHERAPY

(75) Inventors: Franz Gum, Munich (DE); Stephan Froehlich, Aschheim (DE)

(73) Assignee: Brainlab AG, Feldkirchen (DE)

( * ) Notice: Subject to any disclaimer, the term of this patent is extended or adjusted under 35 U.S.C. 154(b) by 102 days.

(21) Appl. No.: 14/235,904

(22) PCT Filed: Aug. 2, 2011

(86) PCT No.: PCT/EP2011/063285
§ 371 (c)(1),
(2), (4) Date: Jan. 29, 2014

(87) PCT Pub. No.: WO2013/017164
PCT Pub. Date: Feb. 7, 2013

(65) Prior Publication Data
US 2014/0171726 A1    Jun. 19, 2014

(51) Int. Cl.
*A61N 5/10*  (2006.01)
*A61B 6/03*  (2006.01)
*A61B 6/00*  (2006.01)

(52) U.S. Cl.
CPC .............. *A61N 5/1039* (2013.01); *A61B 6/032* (2013.01); *A61B 6/4085* (2013.01);
(Continued)

(58) Field of Classification Search
CPC ....... A61N 5/10; A61N 5/103; A61N 5/1031; A61N 5/1048; A61N 5/1049; A61N 2005/1032; A61N 2005/1033; A61N 2005/1035
USPC ......................................... 378/65; 600/1, 411
See application file for complete search history.

(56) References Cited

U.S. PATENT DOCUMENTS

2008/0226030 A1* 9/2008 Otto ................................. 378/65
2011/0103551 A1* 5/2011 Bal .......................... A61N 5/103
                                                            378/65
(Continued)

FOREIGN PATENT DOCUMENTS

EP    0 205 720         12/1986
EP    0205720 A1  *    12/1986
(Continued)

OTHER PUBLICATIONS

International Search Report and Written Opinion for International Application No. PCT/EP2011/063285 dated Apr. 5, 2012.
(Continued)

*Primary Examiner* — Robert Kim
*Assistant Examiner* — David E Smith
(74) *Attorney, Agent, or Firm* — Tucker Ellis LLP

(57) ABSTRACT

The present invention relates to a method for positioning an arrangement of at least one beam position relative to a patient's body when the patient is placed for treatment by means of a treatment device which can emit treatment radiation, wherein the at least one beam position describes at least one position of at least one treatment beam, wherein the arrangement is referred to as the treatment arrangement and the treatment beam comprises the treatment radiation, wherein the method is executed by a computer and comprises the following steps:

providing treatment beam absorption data which describe the absorption properties of the at least part of the body with respect to absorbing the treatment radiation, and the relative position between the at least part of the body and the treatment arrangement;

providing treatment beam data which describe radiation properties of the at least one treatment beam;

providing condition data which describe a condition for treating the at least part of the body;

determining an optimum relative position between the treatment arrangement and the at least part of the body on the basis of the condition data, the treatment beam data and the treatment beam absorption data.

21 Claims, 3 Drawing Sheets

(52) U.S. Cl.
CPC .......... *A61N 5/1031* (2013.01); *A61N 5/1048* (2013.01); *A61N 5/1049* (2013.01); *A61N 5/1077* (2013.01); *A61N 2005/1061* (2013.01)

(56) References Cited

U.S. PATENT DOCUMENTS

| | | | | |
|---|---|---|---|---|
| 2011/0122997 | A1* | 5/2011 | Lu | A61N 5/1031 378/65 |
| 2011/0248188 | A1* | 10/2011 | Brusasco | A61N 5/1048 250/492.1 |
| 2012/0123184 | A1* | 5/2012 | Otto | A61N 5/1067 600/1 |
| 2013/0006093 | A1* | 1/2013 | Raleigh | A61B 5/0037 600/411 |
| 2013/0085735 | A1* | 4/2013 | Vilsmeier | G06F 19/3437 703/11 |
| 2013/0151218 | A1* | 6/2013 | Myles | A61N 5/1049 703/6 |

FOREIGN PATENT DOCUMENTS

| | | | |
|---|---|---|---|
| WO | 2004033027 | 4/2004 | |
| WO | WO 2004033027 A2 * | 4/2004 | ............. A61N 5/103 |
| WO | 2009/156896 | 12/2009 | |

OTHER PUBLICATIONS

Communication pursuant to Article 94(3) EPC for corresponding European Application No. 11 738 244.0 dated Feb. 2, 2015, 9 pages).

* cited by examiner

DOSE-OPTIMISED PATIENT POSITIONING FOR RADIOTHERAPY

This application is a national phase application of International Application No. PCT/EP2011/063285 filed Aug. 2, 2011 and published in the English language.

The present invention is directed to a method for positioning an arrangement of treatment beams, in particular beams of ionising radiation used for radiotherapy, relative to a patient's body.

Volumetric cone beam computed tomography (CBCT) imaging is increasingly becoming a standard for patient positioning in modern radiotherapy. Currently, the CBCT images are manually or automatically fused to a computed tomography (CT) image used for planning a treatment, in particular a radiotherapy treatment. The CBCT image and the CT image are in particular three-dimensional.

The CT image used for treatment planning may not however depict the actual geometry of the patient's body, in particular interior regions of the patient's body, after it has been placed, in particular on a couch, in order for radiotherapy to commence. A risk therefore exists that organs at risk (OAR) may be irradiated by the treatment beam and absorb an undesirably high radiation dose if they are undesirably placed in the beam path between the apparatus used for irradiation (i.e. the treatment device) and the planning target volume (PTV).

Currently used methods for correcting offsets in the position of the patient use a position of the PTV which is derived from a CBCT image taken after the patient has been positioned and before radiotherapy is commenced.

The present invention seeks to solve the problem of optimizing the position of a patient for radiotherapy.

This problem is solved by the subject-matter of any one of the appended independent claims. Advantages, advantageous features, advantageous embodiments and advantageous aspects of the present invention are disclosed in the following and contained within the subject-matter of the dependent claims. Different advantageous features can be combined in accordance with the invention as long as this is technically sensible and feasible.

The method according to the invention is preferably at least partly executed by a computer, i.e. all the steps or merely some of the steps (i.e. less than the total number of steps) of the method according to the invention can be executed by a computer.

The inventors have recognized that deviations from a planned dose distribution occur due to a change in body geometry, for example because internal organs have shifted relative to one another as compared to the body geometry depicted by the treatment planning CT image. This can occur even if the PTV is placed correctly. Changes in body geometry can however also have a significant impact on the actual dose delivered to both the PTV and the OARs. The inventors have in particular recognized that an image taken after the patient has been placed and before the treatment is commenced (i.e. for example the aforementioned CBCT image) includes more information than just the position of the PTV. This additional information can be used to minimise the aforementioned deviations. As will be explained later, the planning image (for instance, the CT image) in particular can be fused with the pre-optimisation image (for instance, the CBCT image) in order to identify the structures (body part elements) defined in the planning image. While the planning image generally exhibits a known relationship between absorption properties and image properties, the pre-optimisation image reflects the actual structure (in particular, the actual position of the body elements) of the patient's body. These two forms of information are preferably combined in order for the position of the patient to be optimised for the treatment, in particular even if deformation of the body structures (body elements) occurs. The optimisation is based in particular on a calculation of doses (in particular dose volume histograms or DVHs, as described below) based on the information included in the pre-optimisation image (and optionally also based on the information included in the planning image). Having highlighted above some aspects of the embodiments of the invention, additional aspects, advantages and the general ideas and features of the invention will be described below.

The present invention relates to the field of medicine and in particular to using (more specifically, to controlling) beams, in particular radiation beams, in order to treat parts of a patient's body. The beams are also referred to as treatment beams. A treatment beam treats body parts which are to be treated, which are referred to in the following as treatment body parts. A region or a collection of regions within which some or in particular all of the treatment body parts are present and which is in particular filled by the treatment body parts is referred to as the target region. The treatment body parts are in particular parts of a patient's body, i.e. anatomical body parts. Ionising radiation is in particular used for the purpose of treatment. In particular, the treatment beam comprises or consists of treatment radiation which is in particular ionising radiation. The ionising radiation comprises or consists of particles (for example, sub-atomic particles or ions) or electromagnetic waves which are energetic enough to detach electrons from atoms or molecules and so ionise them. Examples of such ionising radiation are x-rays, high-energy particles (high-energy particle beams) and/or ionising radiation emitted from a radioactive element. The treatment radiation, in particular the treatment beam, is in particular used in radiation therapy or radiotherapy, in particular in the field of oncology. For treating cancer in particular, parts of the body comprising a pathological structure or tissue such as a tumour are treated using ionising radiation, in particular by irradiating it with the ionising radiation. The tumour is then an example of a treatment body part.

The treatment beam is preferably controlled such that it passes through the treatment body part. However, the treatment beam can have a negative effect on body parts outside the treatment body part. These body parts are referred to here as outside body parts. A region or a collection of regions within which the outside body parts are present and which is in particular filled by the outside body parts is referred to as the off-target region. The OARs are in particular located in the off-target region. Generally, a treatment beam has to pass through outside body parts in order to reach and so pass through the treatment body part, even though it is desirable to irradiate outside body parts as little as possible.

The method according to the invention is preferably a method for positioning an arrangement which is used or is to be used for treatment and which is therefore referred to as a treatment arrangement. The treatment arrangement is an arrangement of at least one beam position and preferably an arrangement of beam positions, i.e. an arrangement of more than one beam position. Properties of the treatment arrangement are described in the following. Preferably, the arrangement represents positions of treatment beams (referred to as "treatment beam positions") which are preferably in a pre-defined, preferably fixed position relative to one another. The terms "fixed" or "keeping fixed" mean that the relative position of the treatment beams as defined by an arrangement referred to as the planned arrangement (which has been defined in accordance with a planning procedure, in particular on the basis of planning image data such as CT images) is identical to the relative position of the treatment beams as defined by the treatment arrangement which is used during (a subsequent) treatment, i.e. the optimum relative position is preferably determined subject to the condition that the relative beam positions of the treatment arrangement (i.e. the treatment beam positions) are identical to the relative beam positions of the planned arrangement (i.e. the planned beam positions).

Where the term "arrangement" alone is used in the following, this refers to properties of the arrangement which apply to the treatment arrangement and the planned arrangement. Where the term "beam positions" alone is used in the following, this refers to properties of the planned beam positions and the treatment beam positions. The terms "pre-optimisation arrangement" and "pre-optimisation beam positions" refer to the treatment arrangement and the beam positions, respectively, at the pre-optimisation time. At the pre-optimisation time, the pre-optimisation arrangement has a relative position with respect to at least part of the body which is referred to as the "pre-optimisation relative position". There can be one or more pre-optimisation times. A pre-optimisation time is a point in time before the optimum relative position is determined in accordance with the invention. The optimum relative position can be determined one or more times before and/or during the treatment. In particular, the optimum position is determined before the treatment (and after the patient has been placed). It is also possible for the body to deform during the treatment. Therefore, the optimum relative position can be determined a plurality of times; in particular, the pre-optimisation images (described further below) can be generated a plurality of times during the treatment in order to determine the optimum relative position a plurality of times on the basis of said pre-optimisation images.

The beam positions describe the positions of the treatment beams of the arrangement. A beam position is preferably defined by the beam direction and additional information which allows a specific location, in particular in three-dimensional space, to be assigned to the treatment beam, such as for example information about the co-ordinates in a defined co-ordinate system. The specific location is one point, preferably on a straight line. This line is referred to as the "beam line" and extends in the beam direction and for instance along the central axis of the treatment beam. The defined co-ordinate system is preferably defined relative to the treatment device or relative to at least part of the patient's body. The position of the planned arrangement, and thus in particular the planned beam positions, is/are in particular described relative to the patient's body or at least part of the body by data which are referred to as planning data. The patient's body or at least part of the patient's body comprises a treatment body part and/or at least one outside body part. Where reference is made to "the body", this term can equally be replaced with "at least part of the body". The arrangement of beam positions comprises (in particular consists of) at least one beam position, in particular a discrete set of beam positions (i.e. for example two or more different beam positions) or a continuous multiplicity (manifold) of beam positions.

Additional optional properties of the arrangement are described in the following. During treatment, one or more treatment beams in particular adopt the treatment beam positions defined by the treatment arrangement, simultaneously or sequentially (the latter in particular when there is only one beam source emitting a treatment beam). If there are multiple beam sources, at least a sub-set of the total number of beam positions can also be adopted simultaneously by treatment beams during the treatment. In particular, one or more sub-sets of the treatment beams can adopt the beam positions of the arrangement in accordance with a pre-defined sequence. A sub-set of treatment beams comprises one or more treatment beams. The full set of treatment beams which comprises one or more treatment beams and adopts all the beam positions defined by the arrangement is also referred to as the radiation arrangement. The radiation arrangement is referred to as the planned radiation arrangement if the at least one treatment beam of the radiation arrangement adopts the at least one beam position defined by the planning arrangement. The radiation arrangement is referred to as the pre-optimisation radiation arrangement if the at least one treatment beam of the radiation arrangement adopts the at least one beam position defined by the optimisation arrangement. The radiation arrangement is referred to as the treatment radiation arrangement if the at least one treatment beam of the radiation arrangement adopts the at least one beam position defined by the treatment arrangement. The radiation arrangement is referred to as the optimum radiation arrangement if the at least one beam position of the radiation arrangement adopts the at least one beam position defined by the optimum arrangement. The pre-optimisation radiation arrangement and the optimum radiation arrangement are preferably identical. Preferably, the planning data describe the planned arrangement and optionally the pre-defined sequence. As mentioned above, the treatment arrangement of the at least one beam position which defines the at least one beam position relative to the treatment device and adopts the determined optimum relative position, in particular during (actual) treatment (in particular during a treatment session which is also referred to as a fraction), is the optimum arrangement. The optimum arrangement is typically, but not necessarily, an arrangement which is such that the beam positions of the arrangement pass through the radiation isocentre of the treatment machine, i.e. the point through which all the treatment beams of isocentric treatment machines intersect.

In particular, the relative positions of at least some and more preferably all of the beam positions of the treatment arrangement are kept fixed, as mentioned above. In accordance with one preferred embodiment, the step of determining an optimum relative position uses a virtual arrangement of beam positions. The beam positions of the virtual arrangement are referred to as virtual beam positions. The relative positions of the virtual beam positions are preferably kept fixed (constant) during the step of determining the optimum relative position. The relative positions of the virtual beam positions are preferably identical to the relative positions of the planned beam positions. In accordance with one preferred embodiment, the relative position between the virtual arrangement and at least part of the body is varied during the step of determining the optimum dose, while the relative positions between the virtual beam positions are kept fixed. Keeping the beam positions of the virtual arrangement fixed while determining the optimum dose results in a faster optimisation process, while still achieving a reliable result.

In accordance with one embodiment, the step of determining the optimum dose comprises a step of determining so-called expected dose data (see below) for the different virtual relative positions between the virtual arrangement and the at least part of the body. The virtual relative positions are referred to as "expected relative positions" and are in particular set so as to be identical to at least one of the pre-optimisation relative position and the optimum relative position. The optimum relative position can be determined on the basis of the determined expected dose data for different virtual positions of the virtual arrangement. Preferably, the optimum arrangement is set so as to be identical to the virtual arrangement used for determining the optimum relative position. Other optimisation procedures can of course also be used to determine the optimum relative position. Before discussing how the expected dose data are determined, the absorption of the treatment beam by the body and the conditions for determining the relative optimum position shall be discussed.

Preferably, treatment beam absorption data are provided which describe the absorption properties of the at least part of the body, in particular the (different) absorption properties for different elements (referred to as "body elements") of the at least part of the body and/or the relative position of these different elements of the at least part of the body. The absorption properties describe in particular the percentage of the energy of the treatment beam which is absorbed by one of the respective body elements per unit volume, in particular as a function of the energy level of the treatment beam. Examples of body elements include in particular the treatment body part and the outside body part. The absorption data describe in particular the absorption properties of the body elements with respect to the treatment radiation, in particular the position and/or geometry (size and/or shape) of the at least part of the body and in particular of the different elements.

The treatment beam absorption data can be provided in different ways. As described above and explained in more detail below, the planning image data and/or the pre-optimisation image data can be used to determine the treatment beam absorption data. Databases can also be used to determine the treatment beam absorption data. Absorption properties of different body elements are for example stored in the database, and the different absorption properties are assigned to the different body elements described by the pre-optimisation image data. To this end, the regions shown by the pre-optimisation image are for example segmented and identified as respectively representing a particular body element. A particular absorption property is stored in the database for each of the particular body elements and retrieved by the method according to the invention. It is thus possible to simulate the at least one treatment beam passing through the body (and thus through the body elements) and the treatment beam energy being absorbed by the body (and thus by the different body elements), and expected dose data for the body (and in particular for the different body elements) can be calculated. Another embodiment for determining the treatment beam absorption data on the basis of in particular the planning image (for example, the CT image) is described further below. The embodiment described further below can be combined with the aforementioned embodiment, in particular by also taking into account absorption properties stored in the database, in order for example to check if the absorption properties determined using the planning image are within usual ranges.

In accordance with the above embodiment, the treatment beam absorption data can be determined solely on the basis of the pre-optimisation image and stored relationship data which describe the relationship between image properties of the pre-optimisation image and absorption properties (without taking into account the planning image). The embodiment described further below is in particular based on both the pre-optimisation image and the planning image and uses a known relationship between image properties of the planning image and absorption properties.

The target region comprises a planning target volume (PTV) which in particular encompasses a pathological structure. A target dose can be applied to the target region and is in particular accumulated in the target region. Within the framework of this invention, the term "dose" refers to the irradiation dose which is delivered by the treatment radiation and can be derived from the energy (energy dose) which is deposited in the irradiated body part. The absorption properties which describe the absorption of the treatment beams by the body can for example be based on information about the density of the irradiated tissue and/or information about the sensitivity of the tissue to the treatment radiation, in particular information about the probability of the tissue developing pathological characteristics due to being irradiated with the treatment beams.

Condition data are preferably provided which comprise information describing at least one condition for treating the at least part of the body. In particular, the condition data describe a condition (referred to as the "dose condition") for achieving an optimum dose applied to the at least part of the body. The term "optimum dose" is understood to mean a dose which fulfils dose conditions, in particular with respect to the planned dose. The dose condition in particular comprises rules for achieving the optimum dose, such as a maximum radiation limit (in particular per dose) for at least one outside body part (for example, an OAR) and/or a minimum radiation limit (in particular per dose) for the treatment body part (PTV). The maximum limit and/or the minimum limit is in particular determined by referring to the planned dose, in particular by setting the limit so as to be equal to the planned dose for the outside body part and the treatment body part, respectively. If it is not possible for the radiation dose to be below the maximum limit and/or above the minimum limit, the dose condition in particular specifies that it be as close as possible to the planned dose as described by the planning data. The dose conditions, in particular the limits, are in particular described using dose-volume histograms or dose-wall histograms, which are known in the field of radiation treatment planning (see for example Wikipedia). Cumulative dose-volume histograms are preferably used, but direct (differential) dose-volume histograms can alternatively or additionally be used (see for example the article "Debunking DVH, A glance at the meaning of dose-volume histograms" by Mary Hare, MSEd, CMD, RT(T)(CT) and Beverly Riley, CMD, RT(T) which may be accessed on the Internet at the following address: www.rt-image.com/content=7304J05C4876948640969A7644A0B0441).

Preferably, the condition data are determined on the basis of the planning data (also referred to as the treatment plan data). The planning data describe in particular the planned dose. Alternatively and preferably additionally, the planning data describe the planned arrangement of the planned beam positions. As mentioned above, a preferred condition described by the condition data stipulates that the relative position of the planned beam positions of the planned arrangement is identical to the relative position of the adjusted beam positions of the adjusted arrangement (which is in the determined optimum relative position relative to the at least part of the body). Planning is preferably performed on the basis of planning image data such as three-dimensional CT images of the at least part of the patient's body, in particular the treatment body part, before the treatment. The planning data preferably result from this planning and in particular include the planning image data. Advantageously, the optimum dose is a dose to be applied to the treatment body part which is high enough to cause the desired treatment effect. Preferably, the optimum dose also represents a dose applied to the outside body parts which is low enough to avoid undesirable effects, in particular pathological changes to the outside body parts which are irradiated, in particular inevitably irradiated. Preferably, the optimum dose therefore takes into account predetermined and in particular planned dose values (described for example by dose-volume histograms) which are to be (maximally or minimally) accumulated in the treatment body part and the outside body parts, respectively. These predetermined dose values are preferably used as boundary conditions for optimizing the dose applied to at least part of the body. As mentioned above, the condition data preferably comprise information about predetermined dose values and/or rules with respect to boundary conditions (limits) which optimize the dose and in particular enable the optimum dose to be achieved. Advantageously, the condition data also comprise information about the probability (risk) of an irradiated body part developing undesirable, in particular pathological characteristics as a result of being irradiated with a specific dose, and of course a rule for minimizing this risk. The condition data preferably also comprise information about whether a specific body part, in particular an outside body part, is allowed to be irradiated or must not be irradiated at all.

An optimum relative position between the treatment arrangement and the at least part of the body is preferably determined on the basis of the condition data and the treatment beam absorption data. In accordance with one embodiment, the optimum relative position can be determined as the position of the treatment arrangement relative to the body; in accordance with another embodiment, it can be determined as the position of the body relative to the treatment arrangement, depending on the co-ordinate system used to determine the optimum relative position. The optimum relative position is in particular a position in which the treatment beams defined by the treatment arrangement irradiate the treatment body part in such a way that at least a desired dose is delivered to the treatment body part, while preferably simultaneously irradiating the at least one outside body part in such a way that at most a desired dose is delivered to the at least one outside body part. The desired dose for the treatment body part and the desired dose for the at least one outside body part are preferably provided in the condition data and in particular correspond to the planned dose. The optimum relative position is therefore determined using information contained in the condition data. Information contained in the treatment beam absorption data is preferably also used to determine the optimum relative position, since the optimum relative position also depends on the absorption of the treatment beams by the body, in particular the at least part of the body. Treatment beam data are preferably also used for this determination, as described below.

Pre-optimisation image data are preferably provided which comprise information describing the pre-optimisation relative position between the pre-optimisation arrangement and the body at the pre-optimisation time at which the pre-optimisation image data are generated. As mentioned above, this can be before and/or during the treatment. The pre-optimisation relative position is preferably the relative position between the arrangement and the body if the body is placed ready for treatment in accordance with a treatment plan, for example when the patient has been placed on a couch and/or in a predefined position relative to the treatment device (and/or the arrangement) used to emit the treatment radiation. The body in particular reaches the pre-optimisation relative position immediately before the radiotherapy treatment is to commence and in particular before the relative position has been changed to correspond to the optimum relative position (if such a change is made). The time at which the at least part of the body is placed in the pre-optimisation relative position is referred to as the pre-optimisation time. The pre-optimisation relative position is preferably used as an initial value for an algorithm for determining the optimum relative position.

The pre-optimisation image data are preferably used to determine body geometry data, for example by means of segmentation. Atlas data describing an anatomical atlas and/or the segmented planning image can be used for the segmenting process. The body geometry data comprise information which describes the geometric structure of the body and in particular a three-dimensional image referred to as the "geometry image". The term "geometric structure of the body" is used here as a generic term to describe in particular the positions of body elements relative to one another and/or the geometry (i.e. for example the size and/or shape) of the body elements, in particular at the pre-optimisation time. The positions of the body elements relative to one another is defined for example by their distance from one another and/or their location in a preferably common co-ordinate system. The body geometry data can for example comprise information which indicates which body element, such as an internal organ, is directly adjacent to another specific body element, which can also represent an internal organ. The body geometry data can for example indicate that the duodenum is adjacent to the stomach. The geometry of the body part is preferably described by the size of the body element (which can be indicated by its volume and/or weight, which can in turn be calculated by adducing information about the density of the body part) and/or the shape of the body element. The term "shape of the body element" is used here as a generic term for the geometric structure of the surface of the body part which can be approximated by a basic geometric shape such as a sphere or a cuboid (in three dimensions) or a circle or a rectangle (in two dimensions) if comparable information is included in the body geometry data.

The body geometry data are preferably determined on the basis of image data, in particular so-called pre-optimisation image data and planning image data as discussed below and/or on the basis of atlas data which describe an anatomical atlas and are suitable for a segmenting process. The body geometry data can for example be generated by modifying segmented planning image data. The segmented planning image data represent the planning image which is segmented (partitioned) into different segments which represent the aforementioned body elements. The segmented planning image described by the segmented planning image data is preferably deformed on the basis of the pre-optimisation image, in particular using image fusion transformations which are also referred to as image morphing transformations. In particular, the planning image is transformed into the pre-optimisation image by changing the geometries of the elements shown in the planning image while keeping the image properties (in particular their brightness) constant. The transformed planning image represents an example of the geometry image described by the body geometry data. In accordance with another embodiment, the non-segmented planning image is transformed so as to generate the geometry image. The image morphing transformation is described in more detail below.

Image morphing transformations are in particular designed to enable a seamless transition from one image to another. The transformation is in particular designed such that one of a first image (in this case, the planning image) and a second image (in this case, the pre-optimisation image) is deformed, in particular in such a way that corresponding structures (in particular, corresponding image elements; in this case, body elements) are arranged at the same position as in the other of the first and second images. The deformed (transformed) image which is transformed from one of the first and second images is in particular as similar as possible to the other of the first and second images. Preferably, (numerical) optimisation algorithms are applied in order to find the transformation which results in an optimum degree of similarity. The degree of similarity is preferably measured by way of a measure of similarity. The parameters of the optimisation algorithm are in particular vectors of a deformation field. These vectors are determined by the optimisation algorithm which results in an optimum degree of similarity. Thus, the optimum degree of similarity represents a condition, in particular a constraint, for the optimisation algorithm. The bases of the vectors lie in particular at voxel positions of one of the first and second images, which is to be transformed, and the tops of the vectors lie at the corresponding voxel positions in the transformed image. A plurality of these vectors are preferably provided, for instance more than twenty or a hundred or a thousand or ten thousand, etc. There are preferably (other) constraints on the transformation (deformation), in particular in order to avoid pathological deformations (for instance, all the voxels being shifted to the same position by the transformation). The constraints include in particular the constraint that the transformation is regular, which in particular means that a Jacobian determinant calculated from a matrix of the deformation field (in particular, the vector field) is larger than zero. The constraints include in particular the constraint that the transformed (deformed) image is not self-intersecting and in particular that the transformed (deformed) image does not comprise faults and/or ruptures. The constraints include in particular the constraint that if a regular grid is transformed simultaneously with the image and in a corresponding manner, the grid is not allowed to interfold at any of its locations. The optimizing problem is in particular solved iteratively, in particular by means of an optimisation algorithm which is in particular a first-order optimisation algorithm, in particular a gradient descent algorithm. Other examples of optimisation algorithms include optimisation algorithms which do not use derivations such as the downhill simplex algorithm or algorithms which use higher-order derivatives such as Newton-like algorithms. The optimisation algorithm preferably performs a local optimisation. If there are a plurality of local optima, global algorithms such as simulated annealing or genetic algorithms can be used. In the case of linear optimisation problems, the simplex method can for example be used.

In the steps of the optimisation algorithms, the voxels are in particular shifted by a magnitude in a direction such that the degree of similarity is increased. This magnitude is preferably less than a predefined limit, for instance less than $\frac{1}{10}$ or $\frac{1}{100}$ or $\frac{1}{1000}$ of the diameter of the image, and in particular about equal to or less than the distance between adjacent voxels. Due in particular to a high number of (iteration) steps, large deformations can be implemented.

The image data are in particular generated using (medical) imaging methods. CBCT is in particular used to generate the pre-optimisation image data, and CT is in particular used to generate the planning image data. The image data of at least parts of the patient's body can for example be provided using medical imaging methods. This is understood to mean radiological methods, advantageously apparatus-based radiological methods (so-called medical imaging modalities), such as for instance computed tomography (CT), x-ray tomography, magnetic resonance tomography (MRT or MRI), conventional x-ray, sonography and/or ultrasound examinations, and positron emission tomography. Further explanations with respect to imaging methods are given below.

Alternatively or additionally, the pre-optimisation relative position described by the pre-optimisation image data is compared with the determined optimum relative position. In particular, a difference between the optimum relative position and the pre-optimisation relative position is determined in order to allow the relative position to be changed between the at least part of the body and the arrangement, in order to move the at least part of the body to the optimum relative position for treatment. To this end, position control data which are designed to control the relative positions between the arrangement and the at least part of the body are preferably determined and in particular outputted.

As mentioned above, the body geometry data can be described by the geometry image which is in particular determined by transforming the planning image. The planning image can have image properties which are directly linked to absorption properties of the body elements shown in the planning image. If, for example, the planning image is a CT image, then the CT image represents the density of the body elements. The absorption properties of the body can be calculated based on the density. To this end, preferably an intensity value is calculated for each voxel of the CT image. The intensity value characterizes the attenuation (in particular absorption) of the x-ray radiation by the body elements. The attenuation is preferably described by a so called CT value which is preferably described in Hounsfield units. That is, the planning image data preferably describe CT-values for the voxels of the CT image. Preferably, the CT-values are assumed to correspond to the absorption properties of the voxels which can be part of the body elements. In particular a linear relationship between the CT-values and the absorption properties is assumed. In order to present a processed CT image to a user, the planning image data are often processed in order to reflect a sub range of the full range of CT-values by brightness values of the processed image. This processing is also called "windowing". As far as herein the term "CT image" is used, it preferably refers to an image which represents the CT values of the voxels and preferably does not refer to the processed CT-image (processed by "windowing"). Preferably, the geometric structure of the body described by the geometry image corresponds to the geometric structure described by the pre-optimisation image. Preferably, at least one image property (such as for example brightness, in particular in the form of a grey scale value) of the body elements corresponds to the image properties of the planning image. The at least one image property preferably has a known relationship to the absorption property of the respective body elements. The treatment beam absorption data can thus be determined on the basis of the geometry image (which is in particular based on the pre-optimisation image and the planning image). Thus, in accordance with one embodiment, the treatment beam absorption data are determined on the basis of the pre-optimisation image data. The treatment beam absorption data can also be determined on the basis of the pre-optimisation image data as in accordance with the embodiment described in the next paragraph.

Preferably, the above-mentioned pre-optimisation image data are used to determine the treatment beam absorption data. To this end, relationship data can preferably be provided which describe a relationship between properties of the pre-optimisation image (in particular, the brightness and/or contrast and/or color of the image) and absorption properties with respect to the treatment beam (treatment radiation). These relationship data can in particular be stored in a database and/or can be determined by comparing the pre-optimisation image with the planning image. The planning imaging data are generated before the patient is placed for the treatment. The planning imaging data are in particular generated using CT, while the pre-optimisation imaging data are in particular generated using CBCT. In particular, a known relationship between radiation absorption and properties of the planning image (described by the planning image data) is transferred to the pre-optimisation image (described by the pre-optimisation image data), in particular by establishing the relationship for the body elements (for example by image morphing or also manually).

In accordance with one embodiment of the invention, the planning image data serve a double purpose, namely on the one hand, to determine the aforementioned relationship data, and on the other hand, to plan the planned arrangement. In accordance with another embodiment, first and second planning image data are provided. The first planning image data are used to determine the relationship data, and the second planning image data are used to plan the treatment, in particular to determine the planned arrangement and/or the relative position of the planned arrangement relative to the at least part of the body.

In accordance with one embodiment, the treatment beam absorption data are determined on the basis of the relationship data and the pre-optimisation image data. The treatment beam absorption data describe the properties of at least part of the body with respect to absorbing the treatment radiation of the beam arrangement. The treatment beam absorption data describe in particular the absorption properties for at least the part of the body through which the at least one treatment beam passes during the treatment. This part of the body can comprise at least parts of several body elements. In particular, the treatment beam absorption data describe the absorption properties spatially resolved, in particular the absorption properties of regions within at least part of the body. A region can be a part of a body element or can comprise one or more body elements and/or one or more parts of body elements. A region can in particular be represented by one volume element only or by more than one volume element described for instance by one or more voxels of the geometry image. In particular, the relative position between the regions and/or their geometry is described by the treatment beam absorption data. The treatment beam absorption data preferably describe the relative position between the at least part of the body and the treatment arrangement (in particular, the pre-optimisation arrangement). This means in particular that the relative position between (at least one of) the regions and the treatment arrangement (in particular, the pre-optimisation arrangement) is described. The treatment beam absorption data describe in particular the absorption by different body elements, in particular the treatment body part and/or the outside body part(s). In particular, the absorption data are designed to allow the absorbed dose to be determined, in particular locally, i.e. for different regions, in particular for different elements of the body, on the basis of the radiation properties of the treatment radiation arrangement. The radiation properties are in particular the energy level (in particular, the energy distribution) of the at least one treatment beam of the treatment radiation arrangement (in particular, the optimum radiation arrangement) and/or the geometry (i.e. for example the size and/or shape) of the at least one treatment beam (for example, the cross-section of the treatment beam) of the treatment radiation arrangement (in particular, the optimum radiation arrangement). Thus, the treatment beam absorption data allow the absorbed dose to be determined for different body parts on the basis of the treatment beam data which describe the radiation properties of the treatment radiation arrangement, i.e. the radiation properties of the at least one treatment beam of the treatment radiation arrangement. In particular, the radiation properties describe the energy level and/or geometry for the at least one treatment beam of the treatment radiation arrangement as a function of time and/or the relative beam positions. The radiation properties of the planned radiation arrangement and the pre-optimisation radiation arrangement and the treatment radiation arrangement (in particular, the optimum radiation arrangement) are preferably identical. A treatment beam or beams defined by one of the arrangements mentioned herein adopt(s) the relative position(s) with respect to each other as defined by the arrangement and in particular adopt a defined position or positions with respect to an object (such as for example the treatment device, the body, etc.) if the position of the arrangement with respect to this object is defined.

The method according to the invention preferably comprises a step of determining expected dose data which comprises information describing an expected dose which is applied to the at least part of the body. The expected dose is expected for the scenario of treating (for example, irradiating) the at least part of the body if the at least part of the body is in a relative position with respect to the treatment arrangement (which is referred to as the expected relative position). The expected dose data describe the expected dose in particular for the scenario in which the at least part of the body is in the optimum relative position (i.e. the expected relative position is equal to the optimum relative position). On the basis of the determined (in particular, calculated) expected dose, it is possible to determine whether a condition described by the condition data is better fulfilled if the at least part of the body is in the optimum relative position than if the at least part of the body is in the pre-optimisation relative position. The condition cannot be better fulfilled but can be equally well fulfilled if the optimum relative position is identical to the pre-optimisation relative position. In particular, the expected dose data are determined (in particular, calculated) if the at least part of the body is in the pre-optimisation relative position. The optimum position is preferably determined on the basis of expected dose data calculated for different relative positions (such as for example pre-optimisation relative positions, the optimum relative position or other relative positions, and preferably at least the pre-optimisation relative position and the optimum relative position). The expected dose data preferably describe a dose distribution within the at least part of the body. In particular, the dose distribution which would be achieved if the at least part of the body were treated in the pre-optimisation relative position is recalculated before (in particular, immediately before) the dose is delivered. The expected dose data preferably comprise information about the dose applied to the at least part of the body if it is treated in the pre-optimisation relative position in accordance with the planning data. The planning data describe in particular the planned arrangement of the beam positions. The planning data preferably include treatment beam data. The treatment beam data describe in particular the planned energy levels of the treatment beams used for the treatment (in particular as a function of time) and/or the planned geometry (i.e. for example the size and/or shape) of the respective treatment beams of the treatment radiation arrangement (in particular also as a function of time). Preferably, the treatment beams of the treatment radiation arrangement are controlled in accordance with the treatment beam data during the treatment. The respective beams of the treatment radiation arrangement and/or the energy level and/or the geometry of the treatment beams are controlled as a function of time in accordance with the treatment beam data. Thus, the expected dose data can in particular be determined (calculated) on the basis of the treatment beam absorption data and the treatment beam data and also on the basis of the expected relative position and the relative beam positions of the treatment arrangement (which are in particular deemed to correspond to the relative positions of the beam positions of the planned arrangement described by the planning data).

The at least part of the body comprises at least one of a target region (a treatment body part) to which a target dose can be applied and an off-target region (at least one outside body part) to which an off-target dose can be applied. The expected dose data therefore advantageously comprise information about the target dose and/or the off-target dose as determined for the scenario of irradiating the at least part of the body in a predetermined position relative to the arrangement. If the at least part of the body comprises a target region only, then preferably only the target dose is determined, and if the at least part of the body comprises an off-target region only, then preferably only the off-target dose is determined. Preferably, therefore, the target dose and/or off-target dose are only determined as applicable.

Preferably, a planned relative position between the at least part of the body and the planned arrangement of beam positions is determined. In particular, a treatment planning process (performed by a treatment planning system before the treatment, for instance on the basis of planning image data such as computed tomography (CT) images) results in a planned relative position between the body and the planned arrangement. Information about the planned relative position between the body and the planned arrangement is preferably contained in the planning data which describe the treatment plan which contains details about the treatment envisaged for the specific patient, such as the planned position of the treatment beams relative to one another (i.e. a planned arrangement) and a planned beam energy level to be selected for use with the planned arrangement in order to apply a planned dose. Preferably, both the planned beam energy level and the planned dose is included in the planning data. The planning data are preferably provided on the basis of the planning image data determined from image data which are preferably contained in a CT image. This CT image is taken at a point in time referred to as the planning time, which is preferably prior to the time at which the body is placed so as to be ready for treatment. In accordance with one embodiment, the condition data comprise the planning data. The planning image data are preferably generated using a device which does not have a known, in particular fixed positional relationship with respect to a treatment device which emits the treatment beams and/or with respect to a couch on which the patient is placed. The pre-optimisation image data are preferably generated using an imaging device which (performs the medical imaging method and) has a known relative positional relationship with respect to the treatment device and/or the couch.

In this application, the term "image morphing" is also used as an example for "image fusion".

In the field of medicine, imaging methods are used to generate image data (for example, two-dimensional or three-dimensional image data) of anatomical structures (such as soft tissues, bones, organs, etc.) of the human body. Medical imaging methods are understood to mean advantageously apparatus-based imaging methods (so-called medical imaging modalities and/or radiological imaging methods), such as for instance computed tomography (CT) and cone beam computed tomography (CBCT; in particular volumetric CBCT), x-ray tomography, magnetic resonance tomography (MRT or MRI), conventional x-ray, sonography and/or ultrasound examinations, and positron emission tomography. Analytical devices are in particular used to generate the image data in apparatus-based imaging methods. The imaging methods are in particular used for medical diagnostics, to analyze the anatomical body in order to generate images which are described by the image data. The imaging methods are in particular used to detect pathological changes in the structures (tissue) of the human body. However, some of the changes in the anatomical structure, in particular the pathological changes, may not be detectable and in particular may not be visible in the images generated by the imaging methods. A tumour for example represents an example of a change in an anatomical structure. If the tumour grows, it may then be said to represent an expanded anatomical structure. This expanded anatomical structure may not be detectable; in particular, only a part of the expanded anatomical structure may be detectable. Primary/high-grade brain tumors are for example usually visible on MRI scans when contrast agents are used to infiltrate the tumour. The MRI scans represent an example of an imaging method. In the case of MRI scans of such brain tumors, the signal enhancement in the MRI images (due to the contrast agents infiltrating the tumour) is considered to represent the solid tumour mass. Thus, the tumour is detectable and in particular discernable in the image generated by the imaging method. In addition to these tumors, referred to as "enhancing" tumors, it is thought that approximately 10% of brain tumors are not discernable on a scan and are in particular not visible to a user looking at the images generated by the imaging method.

The pre-optimisation image data are preferably provided by taking a CBCT image of the at least part of the body. Since the absorption of CBCT beam energy by a body part is non-homogeneous over the cross-section of the CBCT beam cone, treatment beam absorption values determined from the planning image data are advantageously scaled to the actual geometric structure of the body as depicted by the pre-optimisation image data, in order to determine the optimum relative position. The pre-optimisation image data describe a three-dimensional CBCT image of the at least part of the body, in particular if it is in the actual relative position. The CBCT image represents the anatomical structure at the pre-optimisation time at which the CBCT image was generated. The three-dimensional CBCT image represents the anatomical structure which includes the at least part of the body. Preferably, the treatment body part and the at least one outside body part are represented by the CBCT image in a position relative to each other. Preferably, all the body parts through which the treatment beam passes are represented by the planning image and/or the pre-optimisation image.

The abbreviation CBCT stands for cone beam computed tomography, which is in particular used in the field of image-guided radiation therapy. Advantageously, the present invention is directed to this field of image-guided radiation therapy (IGRT). A CBCT device (used to generate the CBCT images) is in particular arranged such that a relative position between the arrangement and the CBCT device is known. The arrangement is in particular set in accordance with the treatment plan in order to adopt a particular position with respect to a treatment device which emits the treatment beam. Preferably, the relative position between the CBCT device and the treatment device is known, as a result of which the relative position between the arrangement and the CBCT device (and therefore the CBCT image) is also known.

In particular, the CBCT image allows the position of the at least part of the body with respect to the treatment arrangement to be determined. Deviations in the pre-optimisation relative position (i.e. the relative position as determined from the CBCT image) of the at least part of the body from its planned relative position (as determined from the CT image) can in particular be determined. In particular, the CBCT device acquires a plurality of projections over the anatomical structure of interest, i.e. the at least part of the body. The two-dimensional projections are in particular reconstructed into a three-dimensional CBCT image (three-dimensional volume) which is in particular matched to the planning image data using reconstruction strategies (as proposed for instance by Feldkamp). One advantage of the three-dimensional CBCT image is that it represents soft tissue parts and therefore allows a three-dimensional CBCT image to be registered to the three-dimensional planning image used for planning (for example, the CT image) and described by the planning image data. Planning is performed on the basis of the planning image and results in a planned relative position of the at least part of the body relative to the planned arrangement.

In general terms, there are several points in time during which different data are generated or during which different actions are taken. At a planning time (which can be several hours or several days before treatment), the planning data—in particular, planning image data—are generated. At a time referred to as the pre-optimisation time, at which the patient has already been placed in the treatment device in order to be treated using the treatment beam, the pre-optimisation image data are generated, in particular using a device which is in a known spatial relationship with respect to the treatment arrangement. In accordance with one embodiment of the invention, the optimum relative position is then determined and the position of the at least part of the body is preferably changed so as to correspond to this optimum relative position. In accordance with another embodiment, the pre-optimisation relative position is compared with the relative position planned for the treatment body part and, if there is a deviation (in particular for example above a predetermined threshold level), the position of the body is changed such that the new position (referred to as the adjusted position) of the at least part of the body corresponds to the relative position which was for example planned for the treatment body part. However, the relative position planned for the treatment body part can result in a sub-optimum dose distribution due to organ deformation. Therefore, in a following step, the optimum relative position is determined and the at least part of the body is preferably changed in order to correspond to the optimum relative position (in particular if the deviation between the adjusted position and the optimum relative position is above a certain threshold level). Thus, it is at the user's discretion to determine a deviation between the pre-optimisation relative position and a relative position planned for a body element and to make an adjustment. After such an adjustment, the adjusted relative position is preferably compared with the optimum relative position in order to optimize the position of the at least part of the body with respect to the treatment arrangement. It is also possible to directly optimize the relative position on the basis of the determined optimum relative position, without an intermediate adjustment.

If the pre-optimisation image data (which describe the pre-optimisation image) do not include all but only some of the part of the body through which the treatment beam passes, the pre-optimisation image can be expanded, in particular extrapolated using the planning image (for example using image fusion) in order to encompass more of the part of the body and in particular all of the part of the body. Preferably, the treatment beam absorption data can be determined on the basis of the expanded pre-optimisation image.

The expected dose data and/or the condition data are preferably described by means of dose volume histograms (DVHs). DVHs are used to summarize three-dimensional dose distributions in a graphic two-dimensional format. In modern radiation therapy, three-dimensional dose distributions are typically created in a computerized treatment planning system on the basis of a 3D reconstruction of a CT scan. The condition data preferably describe the dose condition by means of DVHs. These DVHs are preferably compared with the DVHs of the expected dose data in order to determine whether the conditions are fulfilled.

The volume referred to in DVH analysis can be the treatment body part and/or an outside body part. DVHs can be visualized by way of differential DVHs or cumulative DVHs. A DVH is created by first determining the size of the dose bins of the histogram. The bins are defined per dose interval and can be of arbitrary size, for example 0-1 Gy, 1.001-2 Gy, 2.001-3 Gy, etc. In a differential DVH, the bar or column height indicates the volume of the structure which receives a dose specified by the bin. Bin doses are plotted along the horizontal axis, and structure volumes (relative, i.e. percent, or absolute volumes) are plotted along the vertical axis. A differential DVH has the appearance of a typical histogram. A cumulative DVH is also plotted with bin doses along the horizontal axis, but the column height of the first bin (for example, 0-1 Gy) represents the volume of the structure which receives as much as or more than said dose. The column height of the second bin (for example, 1.001-2 Gy) represents the volume of the structure which receives as much as or more than that dose, etc. If bin sizes are very small and therefore fine, i.e. if the resolution into classes is very high, then the cumulative DVH acquires the appearance of a smooth-line graph, wherein the line always slopes from top-left to bottom-right. The cumulative DVH for a structure receiving a very homogenous dose—for example, 100% of the volume receiving exactly 10 Gy—will appear as a horizontal line at the top of the graph, at the 100% mark as plotted vertically, with a vertical drop at 10 Gy on the horizontal axis. Preferably, DVHs are calculated for at least one of the body elements represented by the planning image and/or the pre-optimisation image and are displayed on a display device (such as a monitor which is connected to a computer running a program which implements the steps of the method) for the corresponding image.

In accordance with one advantageous embodiment, the optimum relative position is determined (fully) automatically. In particular, the relative position is automatically changed to the optimum relative position by technical means such as a movement device (for example, an electric motor) attached to the patient couch and/or the treatment device. To this end, the electronic data processing device provides the movement device with drive data which comprise information about how to drive, in particular rotate the patient couch and/or the treatment device. In accordance with a semi-automatic embodiment, a user can (actually and/or virtually) change, i.e. shift and/or rotate, the relative position manually between the at least part of the body and the position of the treatment arrangement. In particular, the new expected dose—in particular, a new distribution of expected doses—which results from the relative movement can be calculated for elements of the at least part of the body by the electronic data processing device. A changed dose distribution is preferably also then displayed, in particular in the form of DVHs or differential doses for the structure after the movement, and preferably also the inputted dose-volume threshold doses. This supports the user in defining the optimum relative position.

The image property (such as for example the brightness as described using grey scales) of the planning image advantageously comprises information about the image property of discrete parts (for example regions, in particular pixels and/or voxels) of the CT image (i.e. the planning image), in particular information about a grey-scale value of regions, in particular pixels, of the CT image. Such a grey-scale value is advantageously measured in Hounsfield units which are a measure of absorption of ionising radiation by tissue. Combining the pre-optimisation image data with the planning image data allows corresponding geometric structures (in particular, corresponding body elements) to be identified in the pre-optimisation image data and planning image data and allows image information contained in the pre-optimisation image data to be assigned to image information contained in the planning image data. This assignment advantageously allows the absorption values (which for example describe the percentage of the treatment beam energy absorbed) as determined for discrete parts of the planning image data to be assigned to discrete parts of the pre-optimisation image data comprising image information which corresponds to image information contained in the discrete parts of the planning image, thus obtaining information about the beam absorption properties of the parts—in particular, elements—of the at least part of the body. The beam absorption properties are described by the treatment beam absorption data.

If it is determined that the pre-optimisation relative position deviates from the determined optimum relative position, the relative position between the arrangement and the at least part of the body is advantageously changed to the optimum position, for example by moving (rotating and/or translating) the treatment arrangement relative to the body and/or by keeping the position of the treatment arrangement fixed in a global co-ordinate system and moving the patient relative to the treatment arrangement (for example, by moving the couch on which the patient is placed). Preferably, the relative position of the treatment beams relative to one another, as defined by the treatment arrangement, is kept fixed (i.e. constant) while the relative position is changed between the treatment arrangement and the body, in particular while it is changed to the optimum relative position.

Preferably, the optimum relative position is a position in which the expected dose is optimised on the basis of the expected dose data, the condition data and preferably the pre-optimisation image data, in particular preferably also on the basis of the body geometry data. In particular, the optimum relative position is determined such that boundary conditions based on predefined, advantageously desired values for the expected dose, optimum dose and preferably body elements to be irradiated are evaluated. To this end, the expected dose is advantageously compared to a predetermined dose (defined by the condition data). The predetermined dose is advantageously the desired dose (for example, a planned dose which is defined in accordance with the treatment plan) and can alternatively or additionally be a threshold dose which is set in accordance with medical requirements, such as for example a maximum dose which is allowed to be applied to a certain body part, irrespective of the treatment plan. A value for the predetermined dose is advantageously contained in the condition data, such that the aforementioned comparison involves comparing the information contained in the condition data with the information contained in the expected dose data. The predetermined dose can be equal to the optimum dose or can have a predefined relationship with respect to the optimum dose. The predetermined dose can for example be higher or lower than the optimum dose or can lie within a predefined interval below and/or above the optimum dose. If the comparison result is that the expected dose fulfils a predefined criterion with respect to the predetermined dose, then the determined relative position which results in this expected dose is set as the optimum relative position.

Advantageously, an expected dose is not only calculated for the actual relative position. The expected dose can also be calculated for a number of other possible, in particular predetermined relative positions between the at least part of the body and the arrangement, wherein the pre-optimisation relative position can be taken as an initial position and used as a basis for choosing and/or determining said other predetermined positions. The optimum position can then be selected from these predetermined positions, taking into account the boundary conditions imposed by the geometry of the arrangement. This embodiment offers the advantage that a multitude of possible, potential relative positions is considered and the candidate which best fulfils the conditions is selected as the optimum relative position.

In accordance with one embodiment, the expected dose is determined by taking into account determined expected values for the target dose and/or the off-target dose (i.e. by taking into account an expected target dose and/or an expected off-target dose), for example by adding them through linear combination, i.e. by weighting the expected target dose and the expected off-target dose with respect to one another, depending on the therapeutic and pathological (or pathogenic) effects which are to be achieved or, respectively, avoided. The decision as to whether an expected dose is the optimum dose can thus be based on whether or not the expected values for the target dose and the off-target dose have a predetermined relationship.

In accordance with one embodiment, the geometry (for example, the cross-section) of at least one of the treatment beams contained in the arrangement is varied in order to comply with the conditions described by the condition data. The geometry can be varied by varying a collimation geometry which is used to influence the geometry, in particular the cross-section, of the treatment beam and which is therefore advantageously placed in the beam path between the body and the treatment device. The geometry, in particular the cross-section, of at least some of the beams contained in the arrangement can for example be rectangular, triangular or otherwise polygonal. Alternatively or additionally, the cross-section of at least some of the beams contained in the arrangement can be circular or elliptical. Within this context, "varying the geometry" of the beams refers in particular to changing the cross-sectional area of the beam by varying at least some of the geometric quantities which define the shape and/or size of this area, i.e. the basic geometry represented by the cross-section. In the case of a circular cross-section, for example, the cross-section can be varied to a different cross-sectional area by changing the beam radius. In the case of a triangular cross-section, for example, the cross-section can be varied by changing it to a square cross-section, by adding another side to a collimation geometry and changing the angles between the sides to right angles. Thus, both a delimiting geometric structure (appearance) and/or the cross-sectional area of a beam can be varied.

Advantages of the invention which are not at least due to combining the planning image data with the pre-optimisation image data include in particular the fact that a costly re-planning of the treatment due to anatomical changes can be avoided when applying the method according to the invention, since the deformed planning image (represented by the combined image data) can be used as a basis for a treatment plan update or treatment plan change and/or since dose-optimised positioning enables a treatment which fulfils the treatment body part constraints and the outside body part constraints of the initial treatment planning.

The invention also relates to a radiotherapy system comprising a treatment device for generating a treatment beam and a computer on which a program is running or into the memory of which a program is loaded which is configured to cause the computer to perform the method in accordance with the invention. The treatment device is designed to emit the at least one treatment beam as defined by the treatment arrangement and advantageously comprises a particle accelerator and/or an x-ray tube and/or a radioactive source. The treatment device is advantageously designed to move the treatment arrangement relative to the patient's body when the body is being placed for radiotherapy. Alternatively or additionally, a device which serves to place the patient's body, such as a patient couch, can be moved relative to the treatment device. This configuration enables the actual relative position to be changed to the optimum relative position.

The method in accordance with the invention is in particular a data processing method (in particular, for processing image data) which can be embodied by a computer program. The data processing method is preferably performed using technical means, in particular a computer. The computer in particular comprises a processor and a memory in order to process the data, in particular electronically and/or optically. The calculating steps described are in particular performed by a computer. Determining or calculating steps are in particular steps of determining data within the framework of the technical data processing method, in particular within the framework of a program. A computer is in particular any kind of data processing device, in particular electronic data processing device. A computer can be a device which is generally thought of as such, for example desktop PCs, notebooks, netbooks, etc., but can also be any programmable apparatus, such as for example a mobile phone or an embedded processor. A computer can in particular comprise a system (network) of "sub-computers", wherein each sub-computer represents a computer in its own right. A computer in particular comprises interfaces in order to receive or output data and/or perform an analogue-to-digital conversion. The data are in particular data which represent physical properties and/or are generated from technical signals. The technical signals are in particular generated by means of (technical) detection devices (such as for example devices for detecting marker devices) and/or (technical) analytical devices (such as for example devices for performing imaging methods), wherein the technical signals are in particular electrical or optical signals. The technical signals represent in particular the data received or outputted by the computer.

The expression "acquiring data" encompasses in particular (within the framework of a data processing method) the scenario in which the data are determined by the data processing method or program. The meaning of "acquiring data" in particular also encompasses the scenario in which the data are received or retrieved by the data processing method or program, for example from another program, a previous method step or a data storage medium, in particular for further processing by the data processing method or program. Thus, "acquiring data" can also for example mean waiting to receive data and/or receiving the data. The received data can for example be inputted via an interface. "Acquiring data" can also mean that the data processing method or program performs steps in order to (actively) receive or retrieve the data from a data source, for instance a data storage medium (such as for example a ROM, RAM, database, hard disc, etc.) or via the interface (for instance, from another computer or a network). The data can achieve the state of being "ready for use" by performing an additional step before the acquiring step. In accordance with this additional step, the data are generated in order to be acquired. The data are in particular detected or captured (for example, by an analytical device). Alternatively or additionally, the data are inputted in accordance with the additional step, for instance via interfaces. The data generated can in particular be inputted (for instance, into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. Thus, "acquiring data" can also involve commanding a device to obtain and/or provide the data to be acquired. The acquiring step in particular does not involve an invasive step which would represent a substantial physical interference with the body requiring professional medical expertise to be carried out and entailing a substantial health risk even when carried out with the required professional care and expertise. The acquiring step in particular does not involve a surgical step and in particular does not involve a step of treating a human or animal body using surgery or therapy. This also applies in particular to any steps directed to determining data. "Providing first data on the basis of second data" means in particular that the second data are used by the method described herein in order to acquire the first data. In order to distinguish the different data used by the present method, the data are denoted (i.e. referred to) as "XY data" and the like and are defined by the information which they describe.

The invention also relates to a program which, when running on a computer or when loaded onto a computer, causes the computer to perform one or more of the method steps described herein and/or to a program storage medium on which the program is stored (in particular in a non-transitory form) and/or to a computer on which the program is running or into the memory of which the program is loaded and/or to a signal wave, in particular a digital signal wave, carrying information which represents the program, in particular the aforementioned program, which in particular comprises code means which are adapted to perform any or all of the method steps described herein.

Within the framework of the invention, a computer program or computer program elements can be embodied by hardware and/or software (this includes firmware, resident software, micro-code, etc.). Within the framework of the invention, computer program elements can take the form of a computer program product which can be embodied by a computer-usable or computer-readable storage medium comprising computer-usable or computer-readable program instructions, "code" or a "computer program" embodied in said medium for use on or in connection with the instruction-executing system. Such a system can be a computer; a computer can be a data processing device comprising means for executing the computer program elements and/or the program in accordance with the invention. Within the framework of the present invention, a computer-usable or computer-readable medium can be any medium which can include, store, communicate, propagate or transport the program for use on or in connection with the instruction-executing system, apparatus or device. The computer-usable or computer-readable medium can for example be, but is not limited to, an electronic, magnetic, optical, electromagnetic, infrared or semiconductor system, apparatus or device or a medium of propagation such as for example the Internet. The computer-usable or computer-readable medium could even for example be paper or another suitable medium onto which the program is printed, since the program could be electronically captured, for example by optically scanning the paper or other suitable medium, and then compiled, interpreted or otherwise processed in a suitable manner. The computer program product and any software and/or hardware described here form the various means for performing the functions of the invention in the example embodiments. The computer and/or data processing device can in particular include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or vibration element incorporated into an instrument).

In the following, example embodiments of the present invention are described with reference to the figures, which are merely to be regarded as examples of the invention, wherein.

Figure 1:
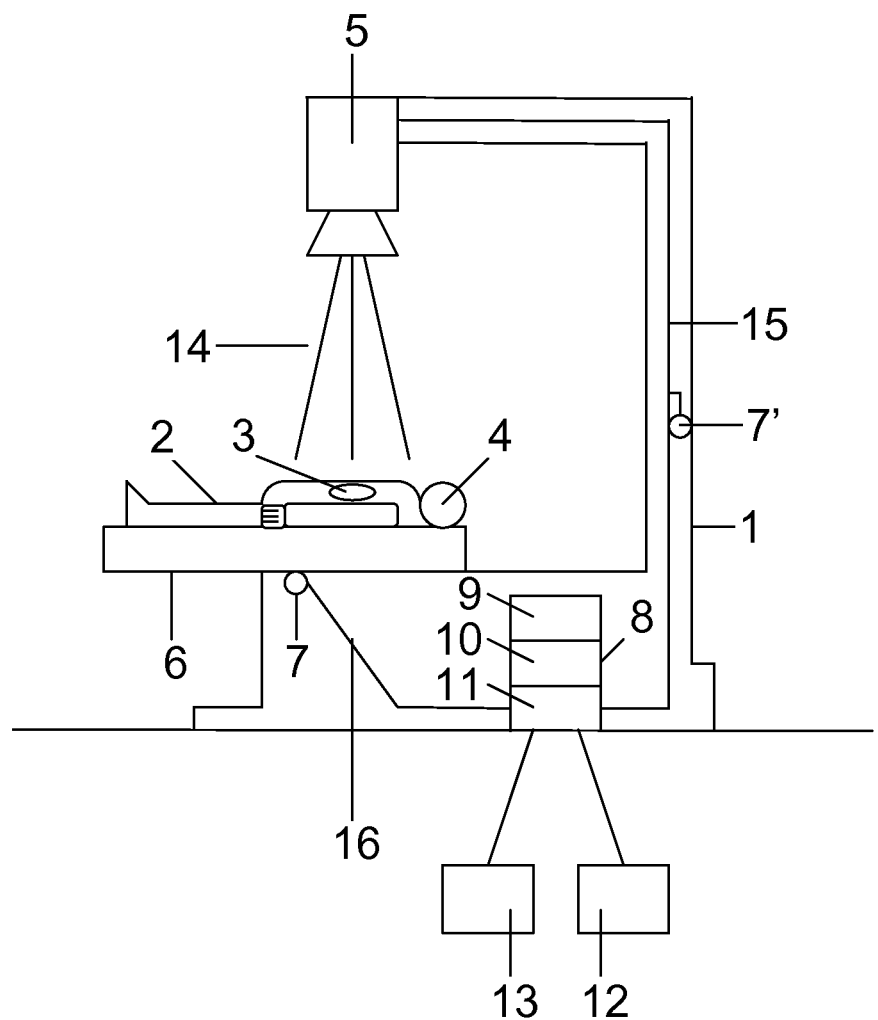
FIG. 1 shows a treatment setup with a patient's body placed ready for treatment by a treatment device.

As shown in FIG. 1, a patient's body 2 comprising a target region 3 and an off-target region 4 is placed on a patient couch 6 of a treatment device 1. The treatment device 1 comprises an irradiation portion 5 which is configured to take a CBCT image of the patient's body and to emit the treatment radiation 14. The treatment device 1 also comprises a motor 7 which is coupled to a transport mechanism of the couch 6 in order to move the patient's body 2 after it has been placed on the couch 6. The treatment device 1 also includes a computer 8 comprising a hard disc 9, a RAM 10 and a CPU 11. The computer 8 is connected by a data line 15 to the irradiation portion 5. The computer 8 is also connected to an input portion 13 and a display unit 12. The input portion 13 preferably comprises a keyboard and a pointing device such as a mouse or a joystick. The display unit 12 preferably comprises a graphic display device such as a monitor and an acoustic output device such as a loudspeaker. The computer 8 is also connected to the electric motor 7 via a data line 16 in order to automatically control the electric motor 7 in moving the couch 6. The treatment device 1 also comprises another electric motor 7' which is also connected to the computer 8 by the data line 15 and is designed to move, in particular shift and/or rotate, the irradiation portion 5 in an absolute co-ordinate system. The electric motor 7' can in particular move the irradiation portion 5 relative to the base of the treatment device 1 and/or relative to the absolute position of the couch 6 and therefore the patient's body 2 if it is placed on the couch 6.

Figure 2:
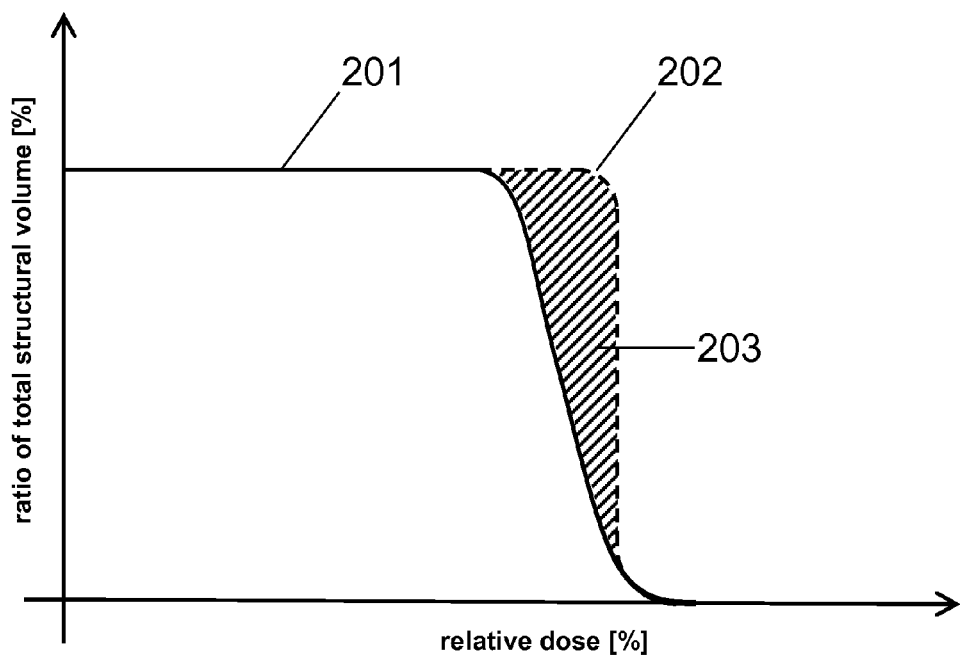
FIG. 2 shows a cumulative dose-volume histogram before and after the relative position is optimised.

FIG. 2 shows a cumulative dose-volume histogram which shows the relative dose received by a specific part of the patient's body—in this case, the target region 3—when irradiated with the treatment radiation 14, plotted against the percentage of the total structural volume of said body part.

Figure 3A:
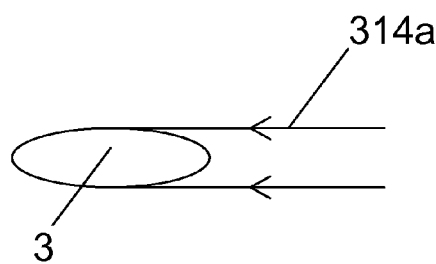
FIG. 3a shows a planned relative position between the planned arrangement of treatment beams and a body part.
Figure 3B:
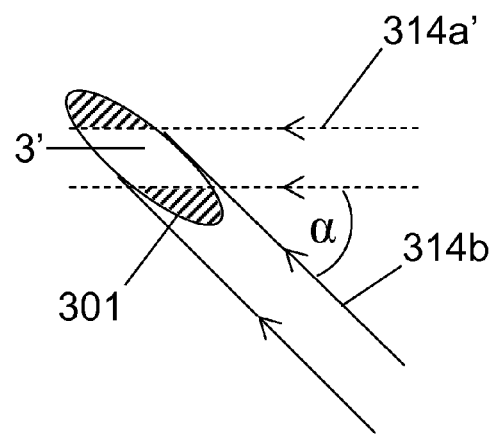
FIG. 3b shows a pre-optimisation relative position and an optimum relative position between the treatment arrangement and a treatment body part.

FIG. 3a shows a planned relative position between a planned arrangement 314a and the target region 3. FIG. 3b shows a pre-optimisation relative position between the target region 3' and the pre-optimisation arrangement 314a'. The target region 3 which has changed its position is denoted in FIG. 3b as the target region 3'. The relative position and the geometry of the target region 3' are known from the pre-optimisation image data.

In the scenario shown in FIG. 3a, the target region 3 is completely covered by the planned treatment beam 314a. The planned dose which is to be received in accordance with the treatment plan by the target region 3 is then equal to the received dose which is arrived at by computing the integral under the curve 202 in FIG. 2. The parts of the target region 3' indicated by shading in FIG. 3b would be outside the coverage of the pre-optimisation treatment beam 314a' as indicated in FIG. 3b and are thus referred to in the following as missed parts 301. The dose received by the target region 3' which is covered by the pre-optimisation treatment beam 314a' then corresponds to the integral under the curve 201 in FIG. 2. This dose is then the aforementioned expected target dose if the expected relative position is equal to the pre-optimisation relative position. A dose corresponding to the integral marked by shading in FIG. 2 and referred to in the following as the missed dose 203 thus represents the difference between the expected dose according to FIG. 3b and the planned dose according to FIG. 3a. The aim of the present method is to achieve a dose in the target region 3' which is equivalent to the integral under the curve 202 in FIG. 2, even though a deformation of the target region 3 may have occurred subsequent to treatment planning. To this end, the pre-optimisation image data and the planning image data are used to determine the optimum relative position, and the position of the treatment beam 314a' is changed, for example by rotating its longitudinal axis by the angle $\alpha$ to the position of the treatment beam 314b which is in the optimum relative position and achieves the desired coverage of the target region 3'. The optimum relative position can be reached by moving the patient's body 2 which is placed on the couch 6, by activating the electric motor 7, or by changing the treatment position of the irradiation portion 5, by activating the electric motor 7'.

Figure 4:
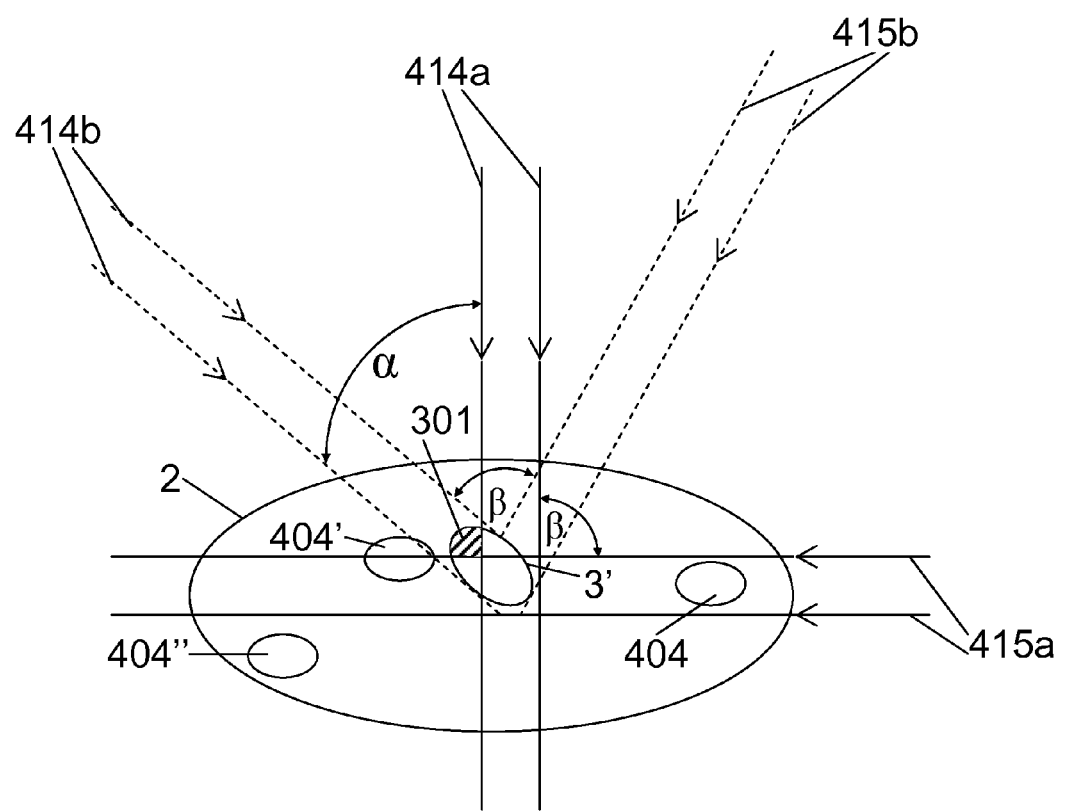
FIG. 4 shows the change in the relative position between the treatment arrangement and treatment body parts and outside body parts, from a pre-optimisation relative position to an optimum relative position.

FIG. 4 shows a cross-section through the patient's body 2 comprising the PTV 3' and OARs 404, 404', 404". Treatment beams 414a, 415a which are directed onto the target region 3' from different—in this case, mutually orthogonal—directions do not cover a missed part 301 of the target region 3' in the configuration shown in FIG. 4. This configuration of at least two treatment beams 414a, 415a constitutes the pre-optimisation arrangement; the configuration of the at least two treatment beams 414b, 415b constitutes the optimum arrangement. The OAR 404 is fully covered by the treatment beam 415a; this illustrates the undesirable scenario that, while body parts which are not to be irradiated (the OARs 404, 404', 404") are covered by the treatment beam 415a, some (the missed part 301) of the body part which is to be irradiated (i.e. the PTV 3') is in fact not covered by the treatment beams 414a, 415a. The method according to the invention is therefore designed to find the optimum relative position between the treatment arrangement on the one hand and the PTV 3' and OARs 404, 404', 404" on the other. As shown in FIG. 4, the treatment arrangement which defines the positions of the treatment beams 414a, 415a is rotated by an angle $\alpha$ such that the optimum relative position of the treatment arrangement which defines the positions of the treatment beams 414b, 415b achieves a full beam coverage of the PTV 3', while as little as possible of the OARs 404, 404', 404" is covered by the treatment beams 414b, 415b. In accordance with a preferred embodiment of the invention, the relative position between the treatment beams 414a, 415a, as indicated by the angle $\beta$, is retained and is in particular kept constant while the treatment arrangement is rotated by the angle $\alpha$. In accordance with another embodiment of the invention, the angle $\beta$ is not kept constant while the treatment arrangement is rotated by the angle $\alpha$, but the angle between the treatment beams 414b, 415b which results at the end of the rotation is once again equal to the initial angle $\beta$ before the rotation. In return for full beam coverage of the PTV 3', a small part of the OAR 404' is covered by the treatment beam 414b. However, the adjusted relative position avoids the complete beam coverage of the off-target region 404 by the treatment beam 415a which obtains in the planned relative position. Consequently, the relative position between the PTV 3', the OARs 404, 404', 404" and the optimum arrangement which defines the positions of the treatment beams 414b, 415b represents an optimum relative position. It is to be noted that some OARs, such as the OAR 404", may not be covered by treatment beams either in the planned relative position or in the optimum relative position.

The terms used in the following description of a second invention and which are identical with the aforementioned terms used in combination with the first invention have the same meaning as described with respect to the first invention.

The present application is also directed to a further independent invention which is directed to the determination of the above-mentioned treatment beam absorption data on the basis of CBCT image data which describe a CBCT image. Preferably, the CBCT image is generated when the patient is placed for treatment. However, it is also possible to generate the CBCT image before placement of the patient. Thus, a preferred embodiment of the invention is as follows:

- A. A method for determining treatment beam absorption data which describe the absorption properties of at least part of a body with respect to absorbing treatment radiation, wherein the method is executed by a computer and comprises the step of determining the treatment beam absorption data based on CBCT image data which describe a CBCT image, wherein the CBCT image comprises a representation of the at least part of the body.
- B. The method according to the aforementioned embodiment A, wherein the CBCT image is generated when a patient is placed for treatment by means of a treatment device which can emit the treatment radiation and wherein an arrangement of at least one beam position is positioned relative to the at least part of the body of a patient and wherein the arrangement is referred to as the treatment arrangement and the treatment beam comprises the treatment radiation, wherein the treatment beam absorption data additionally describe the relative position between the at least part of the body and the treatment arrangement.
- C. The method according to embodiment A or B, wherein the determination of the treatment beam absorption data is further based on relationship data which describe a relationship between properties of the CBCT image and absorption properties with respect to the treatment beam.
- D. The method of one of embodiments A to C, wherein body geometry data are provided which describe position of body elements relative to one another and the geometry of the body elements of the at least part of the body and wherein the relationship data describe the absorption properties of the body elements and wherein the treatment beam absorption data are determined based on the geometry data and based on the relationship data for the body elements of the at least part of the body.
- E. The method of one of embodiments A to D, wherein the treatment beam absorption data are provided additionally on the basis of a CT image, and in particular wherein CT values of the CT image are used to determine absorption values for elements of the body shown in both the CT image and the CBCT image, and in particular wherein the position and geometry of the elements is described by the CBCT image, in particular wherein the CBCT image is generated when the patient is placed for treatment and the CT image is generated before the patient is placed for treatment.
- F. The method of the embodiment D, wherein the absorption properties of the elements of the body (body elements) are determined by fusing (morphing) the CT image and the CBCT image.
- G. The method of the embodiments A to F, wherein a program which when running on a computer (8) or when loaded onto a computer (8), causes the computer (8) to perform the method according to any one of the preceding claims and/or a program storage medium on which the program is stored (in particular in a non-transitory form) and/or a computer (8) on which the program is running or into the memory of which the program is loaded and/or a signal wave, in particular a digital signal wave, carrying information which represents the program, wherein the aforementioned program in particular comprises code which is adapted to perform all the steps of the method according to any one of the preceding claims.
- H. A radiotherapy system comprising the computer according to the preceding embodiment and the treatment device.

According to an aspect of the invention, the treatment beam absorption data are in particular determined when the patient is placed ready for treatment. According to a preferred embodiment, as mentioned above, the treatment beam absorption data are determined based on a CBCT image generated after placement of the patient for treatment and optionally based on a CT image which is generated before placement of the patient for treatment, in particular during the time of planning. However, according to another embodiment, the treatment beam absorption data are determined (additionally or exclusively) based on a CBCT image (in addition to or as an alternative to the CT image generated before placement of the patient for treatment and in addition to or as an alternative to the CBCT image generated after placement of the patient for treatment) which CBCT image is generated before placement of the patient for treatment, in particular during the time of planning. In particular, CBCT images generated at any time considered suitable by a user can be used for determining the treatment beam absorption data.

In particular, the relative position between the at least part of the body and the treatment arrangement is determined based on the relative position between the CBCT image and the treatment arrangement (described by CBCT position data) and in particular also based on the body geometry data (which describe the position of the at least part of the body within the CBCT image).

The invention claimed is:

1. A method for positioning a treatment arrangement of at least one beam position relative to a part of a body of an associated patient when the associated patient is placed for treatment by a treatment device which selectively emits treatment radiation, wherein the at least one beam position describes at least one position of at least one treatment beam, wherein the treatment beam comprises the treatment radiation, wherein the method is executed by a computer and comprises:

a) providing treatment beam absorption data which describe one or more absorption properties of the part of the body with respect to absorbing the treatment radiation, and the relative position between the part of the body and the treatment arrangement;

b) providing treatment beam data which describe one or more radiation properties of the at least one treatment beam;

c) providing condition data which describe a condition for treating the part of the body;
d) determining an optimum relative position between the treatment arrangement and the part of the body based on the condition data, the treatment beam data, and the treatment beam absorption data;
wherein the treatment beam absorption data are provided by determining the one or more absorption properties of the part of the body with respect to absorbing the treatment radiation based on a computed tomography (CT) image and by determining the relative position between the part of the body and the treatment arrangement based on a cone beam computed tomography (CBCT) image.

2. The method according to claim 1, wherein the condition data comprise planning data which describe planned relative positions between the beam positions of a planned arrangement, and wherein the optimum relative position is determined subject to the condition that the relative beam positions of the treatment arrangement are identical to the planned relative positions.

3. The method according to claim 1, wherein image data which are referred to as pre-optimisation image data are provided, which describe an image referred to as the pre-optimisation image which is generated using a medical imaging method at a pre-optimisation time at which the patient is placed for treatment with the treatment beam, and wherein the treatment beam absorption data are determined on the basis of the pre-optimisation image data.

4. The method according to claim 3, wherein the pre-optimisation image data describe a relative position of the treatment arrangement relative to the part of the body, wherein said relative position is referred to as the pre-optimisation relative position and is used to determine the optimum relative position.

5. The method according to claim 1, wherein the treatment beam absorption data describe relative positions between regions of the part of the body and the absorption properties of the regions.

6. The method according to claim 1, wherein the treatment beam absorption data describe the radiation properties of elements of the at least part of the body and relative positions between the elements of the at least part of the body, wherein one of these elements is the at least part of the body to be treated and is referred to as the treatment body part.

7. The method according to claim 6, wherein the relative positions of the elements of the part of the body are determined on the basis of planning image data which describe an image of the part of the body which shows the at least part of the body segmented into the elements, wherein the planning image is generated at a time referred to as the planning time, before the part of the body is placed for the treatment.

8. The method according to claim 7,
wherein image data which are referred to as pre-optimisation image data are provided, which describe an image referred to as the pre-optimisation image which is generated using a medical imaging method at a pre-optimisation time at which the associated patient is placed for treatment with the treatment beam, and wherein the treatment beam absorption data are determined on the basis of the pre-optimisation image data;
wherein the planning image is used to supplement the pre-optimisation image if the pre-optimisation image does not show all the parts through which the at least one treatment beam will pass, wherein the treatment beam absorption data are determined on the basis of the supplemented pre-optimisation image.

9. The method according to claim 1, further comprising:
determining expected dose data which describe an expected dose which is applied to the part of the body, wherein the expected dose is the dose which is expected if the part of the body is in a position relative to the treatment arrangement which is referred to as the expected relative position and is treated by the treatment beam, wherein the expected dose data are determined on the basis of the treatment beam absorption data, the expected relative position and the treatment beam data.

10. The method according to claim 9, wherein the expected relative position is varied in order to determine the expected doses for different expected positions, and wherein the optimum relative position is determined by comparing the different expected doses with the conditions described by the condition data.

11. The method according to claim 9, wherein the part of the body comprises at least one of a target region for which an expected target dose is to be determined and an off-target region for which an expected off-target dose is determined if the treatment arrangement is in the expected relative position, and wherein the condition data comprise conditions for the target region and the off-target region.

12. The method according to claim 1, wherein the treatment beam absorption data are provided based on CBCT image data which describe the CBCT image.

13. The method according to claim 12, wherein the treatment beam absorption data are provided additionally based on the CT image, and wherein CT values of the CT image are used to determine absorption values for elements of the body shown in both the CT image and the CBCT image, and wherein position and geometry of the elements is described by the CBCT image, wherein the CBCT image is generated when the associated patient is placed for treatment and the CT image is generated before the associated patient is placed for treatment.

14. A non-transitory computer readable storage medium comprising a program for positioning a treatment arrangement of at least one beam position relative to a part of a body of an associated patient when the associated patient is placed for treatment by a treatment device which selectively emits treatment radiation, wherein the at least one beam position describes at least one position of at least one treatment beam, wherein the treatment beam comprises the treatment radiation, the program being constituted, when running on a computer or when loaded onto a computer, to cause the computer to perform steps comprising:
a) providing treatment beam absorption data which describe one or more absorption properties of the part of the body with respect to absorbing the treatment radiation, and the relative position between the part of the body and the treatment arrangement;
b) providing treatment beam data which describe one or more radiation properties of the at least one treatment beam:
c) providing condition data which describe a condition for treating the part of the body;
d) determining an optimum relative position between the treatment arrangement and the part of the body based on the condition data, the treatment beam data, and the treatment beam absorption data
wherein the treatment beam absorption data are provided by determining the one or more absorption properties of the part of the body with respect to absorbing the treatment radiation based on a computed tomography (CT) image and by determining the relative position between the part of the body and the treatment arrangement based on a cone beam computed tomography (CBCT) image.

15. A computer comprising the non-transitory computer readable storage medium of claim 14.

16. A radiotherapy system comprising the computer according to claim 15 for positioning the arrangement of the at least one beam position relative to the at least part of the body when the associated patient is placed for treatment by means of the treatment device, the treatment device being designed to emit the at least one treatment beam as defined by the treatment arrangement.

17. A system comprising the computer according to claim 15, the system being operable to position the arrangement of the at least one beam position relative to the part of the body when the associated patient is placed for treatment by means of the treatment device.

18. A method for positioning a treatment arrangement of at least one beam position relative to a part of a body an associated patient when the associated patient is placed for treatment by a treatment device which selectively emits treatment radiation, wherein the at least one beam position describes at least one position of at least one treatment beam, wherein the treatment beam comprises the treatment radiation, wherein the method is executed by a computer and comprises:
   a) providing treatment beam absorption data which describe the one or more absorption properties of the part of the body with respect to absorbing the treatment radiation, and the relative position between the part of the body and the treatment arrangement;
   b) providing treatment beam data which describe one or more radiation properties of the at least one treatment beam;
   c) providing condition data which describe a condition for treating the part of the body;
   d) determining an optimum relative position between the treatment arrangement and the part of the body based on the condition data, the treatment beam data, and the treatment beam absorption data;
   wherein the condition data comprise planning data which describe planned relative positions between the beam positions of a planned arrangement, and wherein the optimum relative position is determined subject to the condition that the relative beam positions of the treatment arrangement are identical to the planned relative positions.

19. A non-transitory computer readable storage medium comprising a program for positioning a treatment arrangement of at least one beam position relative to a part of a body of an associated patient when the associated patient is placed for treatment by a treatment device which selectively emits treatment radiation, wherein the at least one beam position describes at least one position of at least one treatment beam, wherein the treatment beam comprises the treatment radiation, the program being constituted, when running on a computer or when loaded onto a computer, to cause the computer to perform steps comprising:
   a) providing treatment beam absorption data which describe one or more absorption properties of the part of the body with respect to absorbing the treatment radiation, and the relative position between the part of the body and the treatment arrangement;
   b) providing treatment beam data which describe one or more radiation properties of the at least one treatment beam;
   c) providing condition data which describe a condition for treating the part of the body;
   d) determining an optimum relative position between the treatment arrangement and the part of the body based on the condition data, the treatment beam data, and the treatment beam absorption data;
   wherein the condition data comprise planning data which describe planned relative positions between the beam positions of a planned arrangement, and wherein the optimum relative position is determined subject to the condition that the relative beam positions of the treatment arrangement are identical to the planned relative positions and wherein the absorption data are provided by determining the absorption properties of the part of the body with respect to absorbing the treatment radiation on the basis of a computed tomography (CT) image and by determining the relative position between the part of the body and the treatment arrangement on the basis of a cone beam computed tomography (CBCT) image.

20. A computer comprising the non-transitory computer readable storage medium of claim 19.

21. A radiotherapy system comprising the computer according to claim 20 for positioning the arrangement of the at least one beam position relative to the at least part of the body when the associated patient is placed for treatment by means of the treatment device, the treatment device being designed to emit the at least one treatment beam as defined by the treatment arrangement.

* * * * *